United States Patent [19]
Sutter et al.

[11] Patent Number: 5,882,200
[45] Date of Patent: Mar. 16, 1999

[54] DEVICE FOR CONNECTING A DENTAL IMPLANT TO A CONICAL SECONDARY ELEMENT

[75] Inventors: Franz Sutter, Niederdorf; Françis J. Sutter, Hölstein, both of Switzerland

[73] Assignee: Institut Straumann AG, Waldenburg, Switzerland

[21] Appl. No.: 913,537
[22] PCT Filed: Mar. 15, 1996
[86] PCT No.: PCT/CH96/00100
    § 371 Date: Sep. 16, 1997
    § 102(e) Date: Sep. 16, 1997
[87] PCT Pub. No.: WO96/29020
    PCT Pub. Date: Sep. 26, 1996

[30] Foreign Application Priority Data

Mar. 20, 1995 [CH] Switzerland .................. 00783/95

[51] Int. Cl.[6] .................................................. A61C 8/00
[52] U.S. Cl. ............................................................ 433/173
[58] Field of Search ................................ 433/172, 173, 433/174

[56] References Cited

U.S. PATENT DOCUMENTS

| 2,258,207 | 10/1941 | Irwin. | |
| 4,872,839 | 10/1989 | Brajnovic | 433/173 |
| 5,006,068 | 4/1991 | Lee et al. | 433/173 X |
| 5,006,069 | 4/1991 | Lazzara et al. . | |
| 5,026,285 | 6/1991 | Durr et al. | 433/173 |
| 5,071,351 | 12/1991 | Green, Jr. et al. | 433/173 |
| 5,104,318 | 4/1992 | Piche et al. . | |
| 5,145,371 | 9/1992 | Jorneus | 433/173 |
| 5,246,370 | 9/1993 | Coatoam . | |
| 5,779,481 | 7/1998 | Aires | 433/173 |

*Primary Examiner*—Nicholas D. Lucchesi
*Attorney, Agent, or Firm*—Selitto & Associates

[57] ABSTRACT

The significant inventive measure of the arrangement for connecting an implant (1) to the conical secondary part (800) consists in the fact that a radially encircling shoulder part (860) is provided on the conical pillar (830), which shoulder part bears, in the form of an circular ring and partially, on the implant shoulder (14), while the remaining surface on the implant shoulder (14) is covered by the mating shoulder (301) of the impression cap (300) or the crown cap. The shoulder part (860) and the mating shoulders (301) are of complementary configuration to the implant shoulder (14). The connection arrangement can be used in particular in conjunction with a novel plug connection. Further advantages consist in the higher precision in dentistry work which can be achieved without any increased production outlay.

15 Claims, 3 Drawing Sheets

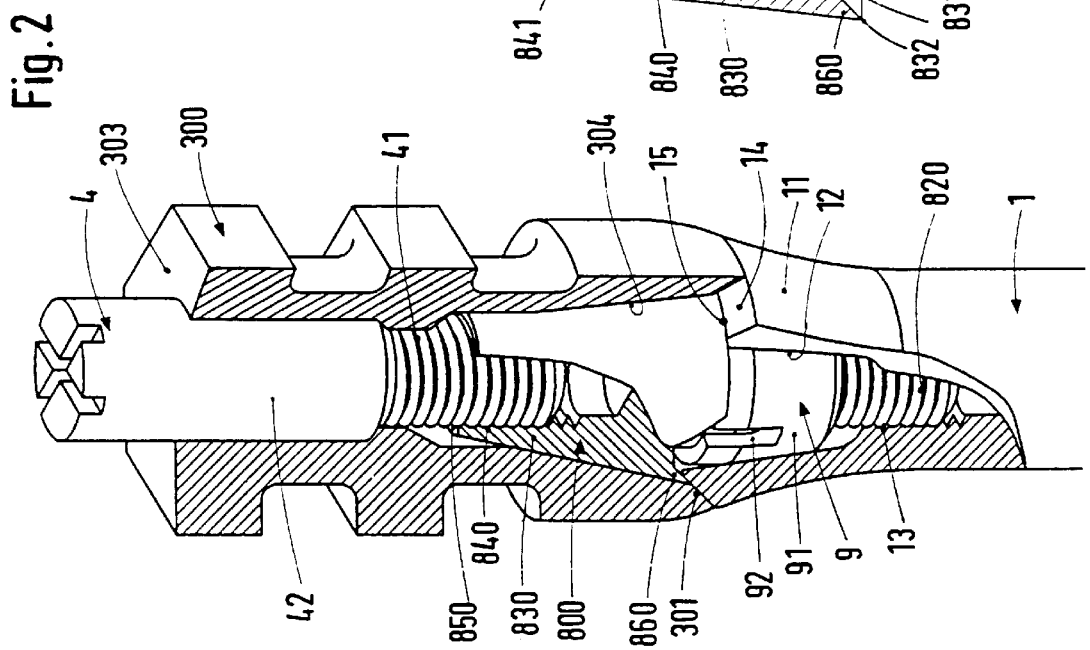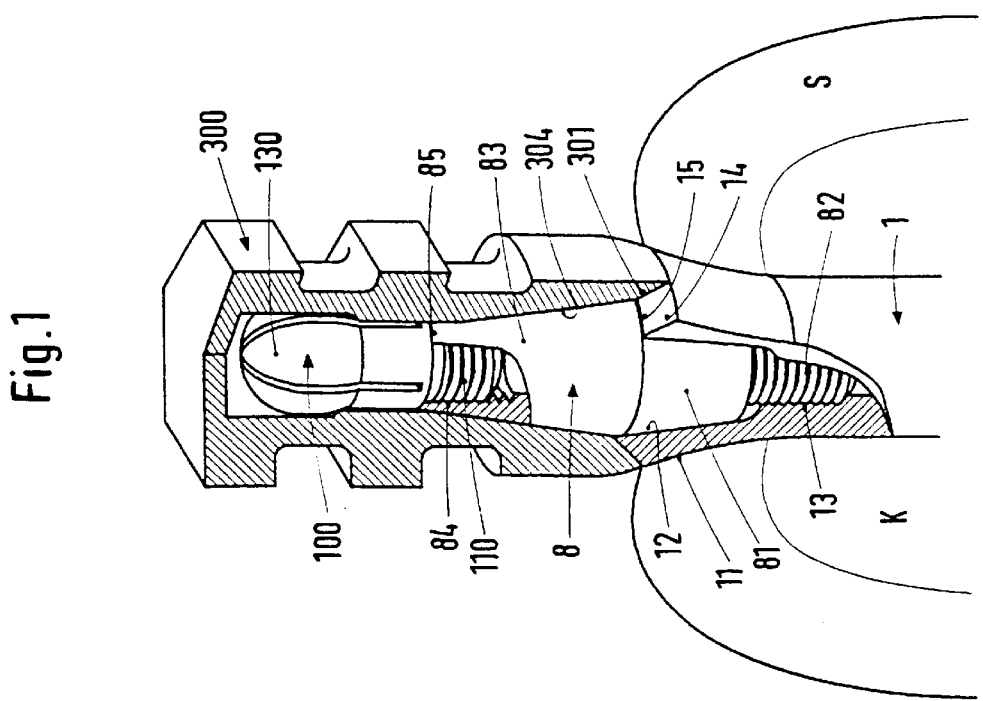

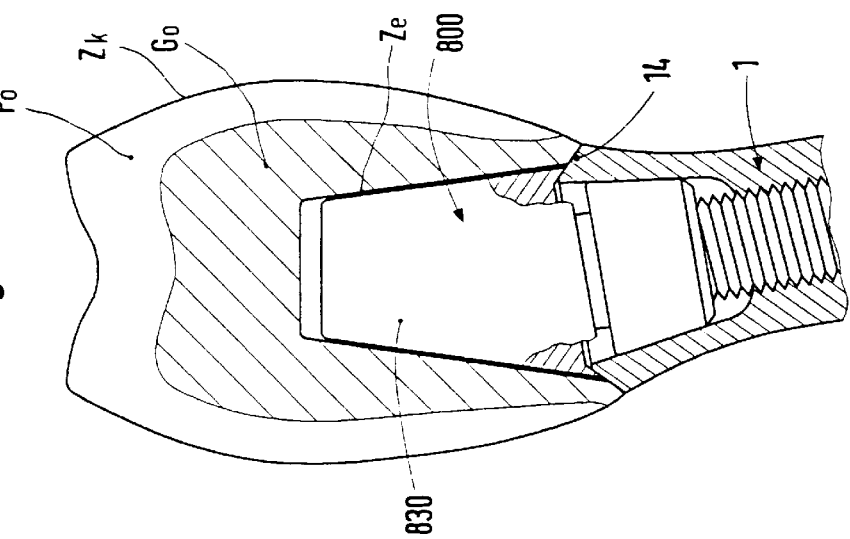
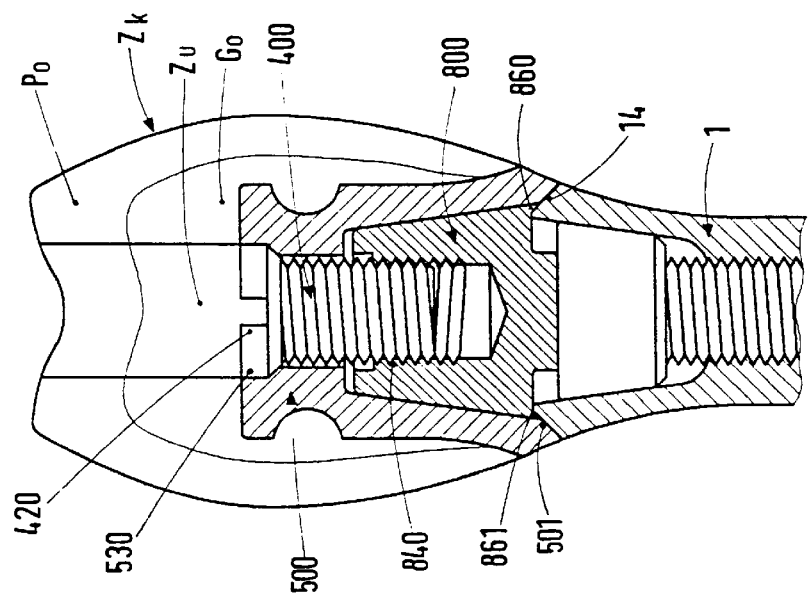
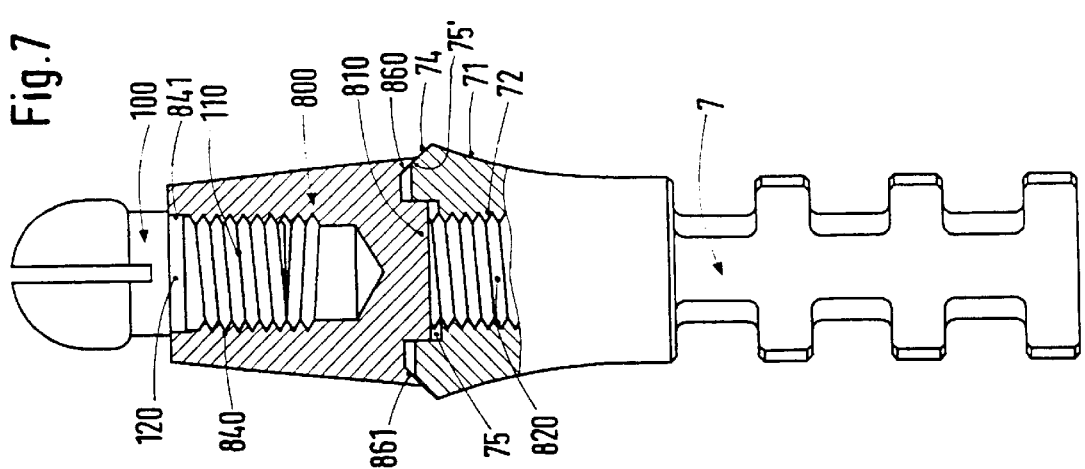

DEVICE FOR CONNECTING A DENTAL IMPLANT TO A CONICAL SECONDARY ELEMENT

The present invention relates to an arrangement for connecting a dental implant and an associated conical secondary part, which can be used for impression taking, producing the master model or fastening a supra-appliance to the implant inserted in the jaw bone.

Constant development in material research, design, in instruments and implantation techniques have resulted in a continuous improvement in the success rate, so that ever more people with missing teeth or even tooth roots which are no longer present are deciding to have implants inserted. As a result, the people in question are able to improve their quality of life. Following bone healing phase of the implant or of a plurality of inserted implants in the jaw bone, the intra-oral geometry has to be transferred in a manner true to the original onto a master model by means of impression taking. The dental technician then uses the master model to produce the dental prosthesis or the artificial single tooth, which are ultimately placed on the existing implants as a supra-appliance in the mouth of the patient. To ensure that this supra-appliance functions without problems over a period of years, it is imperative that all the work, as well as the implants and further components of the system, be implemented highly precisely. This invention is concerned with improving the design of the connection arrangement between an implant and a secondary part which can be inserted into the latter. Depending on the prevailing circumstances, the use of a polygonal secondary part, for example known as octagonal secondary part, or of a conical secondary part may be suitable for the two-part implants in question, comprising the primary part, the actual implant and the secondary part. The conical secondary part in particular forms the subject-matter of the present invention.

Prior art

FIG. 1 illustrates a conventional connection arrangement between an implant and a conical secondary part, as is described, for example, by Schroeder, A. et al. in: Orale Implantologie. [Oral Implantology], Georg Thieme Verlag Stuttgart, 2nd Edition, 1994, p. 199ff. To supplement the illustration, a new type of plug-in anchor and an associated impression cap are also provided, but these form the subject-matter of another patent application, although they can be used particularly advantageously in combination with the connection arrangement to which the present application relates.

FIG. 1

The implant 1 is inserted intraosseously and transgingivally in the upper or lower jaw bone K, so that the implant head 11 penetrates through the mucous membrane S. After the bone healing phase of the implant 1, which lasts 3–4 months, the healing cap which was then no longer visible, was removed and the conical secondary part 8 was screwed into the implant 1 in situ. The base cone 81 of the conical secondary part 8 thus rests in the implant cone 12 and the threaded segment 82 of the conical secondary part 8 engages into the threaded bore 13 of the implant 1. The threaded bore 13 extends out of the chamber of the implant cone 12, axially downwards from the bottom face of the latter. The conical pillar 83 of the conical secondary part 8 protrudes beyond the implant shoulder 14. The transition between the base cone 81 and the conical pillar 83 is situated at the level of the inner edge 15 of the implant shoulder 14. In a manner corresponding to the implant cone 12, the base cone 81 narrows downwards, while the conical pillar 83 narrows upwards. An axial, blind-bore-like threaded bore 84, into which the threaded segment 110 of a plug-in anchor 100 is screwed, extends from the conical-pillar shoulder 85. For the purpose of impression-taking, an impression cap 300 is placed over the plug-in anchor 100 and the conical pillar 83, the mating shoulder 301, which is complementary to the implant shoulder 14, of the impression cap 300 resting completely and without gaps on the implant shoulder 14. The clamping head 130 of the plug-in anchor 100 forms a plug-in connection with the impression cap 300, so that the mating shoulder 301 is virtually pressed onto the implant shoulder 14. The implant shoulder 14 has an outwardly descending chamfer of 45°, measured with respect to the horizontal. A correspondingly complementary chamfer is provided on the mating shoulder 301. To accommodate the conical secondary part 8, the impression cap 300 has a conical bore 304 which continues as a blind-bore-like cavity for accommodating the plug-in anchor 100.

The following statement applies to the whole of the rest of the description. If a figure, in order to produce an unambiguous drawing, contains reference numerals which are not explained in the immediately associated text, reference is made to where they are mentioned in preceding descriptions of figures.

The previous connection arrangement between the implant 1 and the conical secondary part 8 inserted therein and the impression cap 300 then attached or the crown cap subsequently attached was ultimately unable to satisfy the quest for perfection. Even the introduction of a centring sleeve into the implant cone 12 did not provide an optimum solution. Conventional designs have a series of criteria which are worth improving, in particular, for example:

The cone angle of the implant cone 12 is, for example, 8° and the base cone 81 has a corresponding conicity, so that even a tolerance of 0.02 mm leads to an axial displacement of the conical secondary part 8 of 0.18 mm. This relatively large axial displacement may cause undesirable inaccuracies. Thus it is not possible to define very accurately the thickness of the layer of cement between the supra-appliance, when the latter is placed on the implant 1, and the projecting conical pillar 83.

It would be desirable to increase further the accuracy of fit between the conical pillar 83 and the impression cap 300, so that the subsequently produced crown cap as a base for the crown structure could also be designed even more precisely.

The conical pillar 83 provides only a limited contact surface for fixing the crown structure. An enlarged contact surface would permit greater adhesive strength and thus a more stable positioning of the crown structure on the implant 1.

The distribution of the moments of load in the event of high physiological stressing of the crown structure, in particular in the event of lateral and oblique loading, is currently not yet optimally solved.

Hitherto, a considerable effort has been required to produce angled conical secondary parts 8.

In view of the imperfections of the prior art described above, the object of the invention is to provide a connection arrangement between an implant and the conical secondary part 8 screwed into the latter and also the attached impression cap or subsequently applied crown cap which is improved in a large number of respects. It is important here to develop the elements further such that the precision of impression-taking, of the crown structure produced and, finally, of the positioning of the crown is increased, yet the effort required to manufacture the elements can be reduced. Furthermore, it is intended to configure the distribution of forces in the event of extreme stressing of the crown structure more favourably by means of design measures and, finally, it is intended for a modern plug-in connection to be advantageously useable.

The solution to this object is defined by means of the characterizing features of the present invention which includes preferred variant embodiments The essence of the invention consists in the fact that a radially surrounding shoulder part, which, from the inner edge of the implant shoulder, rests in the manner of a circular ring and partially on the implant shoulder, is provided on the conical pillar of the conical secondary part. The remaining surface on the implant shoulder is covered by a tapered mating shoulder of the impression cap or the crown cap. The shoulder part of the conical secondary part and the respective mating shoulder are configured in a complementary manner to the implant shoulder, so that a gap-free positioning can be achieved. Both rotationally symmetrical and angled conical secondary parts are provided with the specially configured shoulder part. The conical secondary parts according to the invention can be employed equally well in implants and in the manipulation implants used in the production of the master model and offer the following essential advantages over the prior art:

The partial bearing of the shoulder part of the conical secondary part on the implant shoulder brings about a centring of the secondary part, tolerances causing a substantially smaller axial displacement. Consequently a more precise configuration is achieved in the entire dental procedure.

Increasing the external diameter of the conical pillar results in a larger contact surface and thus a more stable fixing of the cemented-on crown structure.

The impression-taking of implants positioned in the mouth of the patient can be carried out using a conventionally screwed-on impression cap, but can also be carried out particularly advantageously using a recently developed plug-in connection.

There is total flexibility in the type of crown connection right up until the conclusion of the work. For example, the crown or bridge appliance may be realized by cementing, occlusal screwing, transverse screwing or a plug-in connection.

In particular lateral loads which act on the supra-appliance are taken up in a more effective manner and the production of the secondary part is simplified.

The connection arrangement according to the invention is described in more detail below with reference to the appended drawings, in which:

FIG. 1 shows a partial section through an intraosseously positioned dental implant with a conventional conical secondary part (prior art) and with a modern plug-in anchor and impression cap;

FIG. 2 illustrates a partial section through an implant with a conical secondary part according to the invention, a centring sleeve and an impression cap fixed by means of a positioning screw;

FIG. 3 shows the conical secondary part in accordance with FIG. 2 in detail;

FIG. 7 shows a manipulation implant with the conical secondary part in accordance with FIG. 2 and a plug-in anchor screwed into it;

FIG. 8 shows the connection arrangement with occlusal fastening of the finished crown on the implant, and FIG. 9 shows the connection arrangement with cemented-on fastening of the finished crown to the implant, in an angled version.

FIGS. 2 and 3

Figure 6:
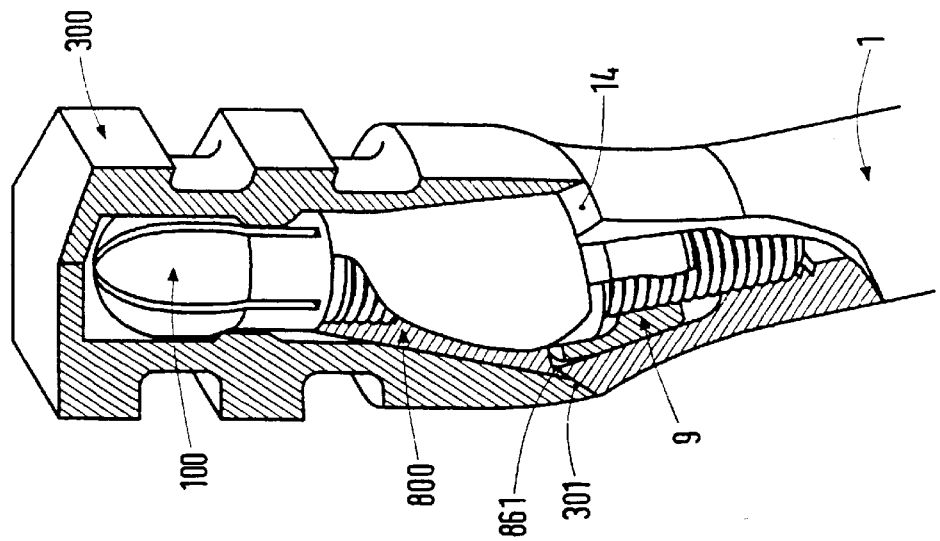
FIG. 6 shows the connection arrangement in accordance with FIG. 5 in an angled version.

The connection arrangement according to the invention for impression-taking essentially comprises the implant 1 inserted in the jaw bone, the conical secondary part 800 screwed into the latter, the centring sleeve 9 resting in the implant cone 12 and the impression cap 300 screwed on by means of positioning screw 4.

The narrowed, cylindrical base pillar 810 of the conical secondary part 800 is accommodated by the centring sleeve 9, which has the sleeve shell 91 with the expansion slots 92. The threaded segment 820 of the conical secondary part 800 is screwed into the threaded bore 13 situated in the implant 1. The conical pillar 830, which at the top ends with the conical-pillar shoulder 850 and at the underside ends with the shoulder part 860, projects beyond the implant shoulder 14. An axial and blind-bore-like threaded bore 840, which is intended to accommodate the threaded segment 41 of the positioning screw 4, extends from the conical-pillar shoulder 850. A groove 831 is made on the underside of the conical pillar 830, so that the shoulder part 860 is formed, which has a conically downwardly opening annular face 861, which runs towards the lower outer edge 832 of the conical pillar 830. The size and angle of inclination of the radially encircling annular face 861, as well as the distance of the latter from the vertical axis, are dimensioned such that the shoulder part 860 rests on the inner zone of the implant shoulder 14 and the annular face 861 comes to bear without gaps against a circular-ring-like sector of the implant shoulder 14. The groove 831 in the underside of the conical pillar 830 is made to be at least sufficiently deep for the inner edge 15 of the implant shoulder 14 not to butt against the limits of the groove 831 over a tolerance range to be observed. By comparison with conventional conical secondary parts, the conical secondary part 800 according to the invention has a thickened conical pillar 830 which engages over the implant shoulder 14.

On the outside, the impression cap 300 has the normal contour with the ribs 303. The particular feature of the impression cap 300 consists in the widened conical bore 304, in order to accommodate the thickened conical pillar 830. At the bottom, the impression cap 300 ends with a tapered mating shoulder 301 which is complementary to the implant shoulder 14, so that the annular face 861 rests on the inside of the implant shoulder 14 and the mating shoulder 301 rests on the outside of the implant shoulder 14. In a manner known per se, the impression cap 300 has an inner seat to accommodate the lower part of the screw head 42 of the positioning screw 4.

At the exit of the threaded bore 840, on the side of the conical-pillar shoulder 850, it is possible to provide a countersinking 841, into which the cylindrical shank segment of an optionally screwed-in plug-in anchor partially engages.

FIG. 4

The particular feature of this embodiment by comparison with FIG. 2 consists in the fact that an angled conical secondary part 800 is now provided instead of a rotationally symmetrical conical secondary part. An angled conical secondary part 800 is used to compensate for the inclined position of an implant 1 positioned in this way owing to the special bone environment. The contours of the annular face 861 and of the mating shoulder 301 are designed to match the angle of the conical secondary part 800, so that in this version too a gap-free positioning is achieved.

FIG. 5

The difference between this figure and FIG. 2 is that an impression cap which is closed at the top, is of modern design, and can be fixed using a plug-in anchor 100, is used instead of the impression cap 300 which can be fixed by means of a positioning screw 4. To this extent, reference is made to the explanation given with regard to FIG. 1. The design of the conical secondary part 800 used corresponds to the illustration in accordance with FIG. 3.

FIG. 6

Figure 5:
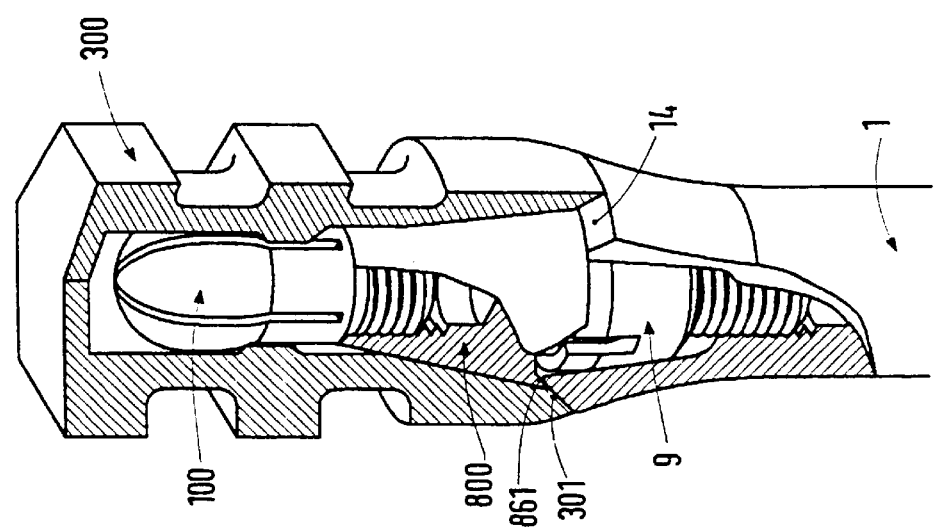
FIG. 5 shows the connection arrangement in accordance with FIG. 2, but with an impression cap fixed by means of a plug-in anchor.
Figure 4:
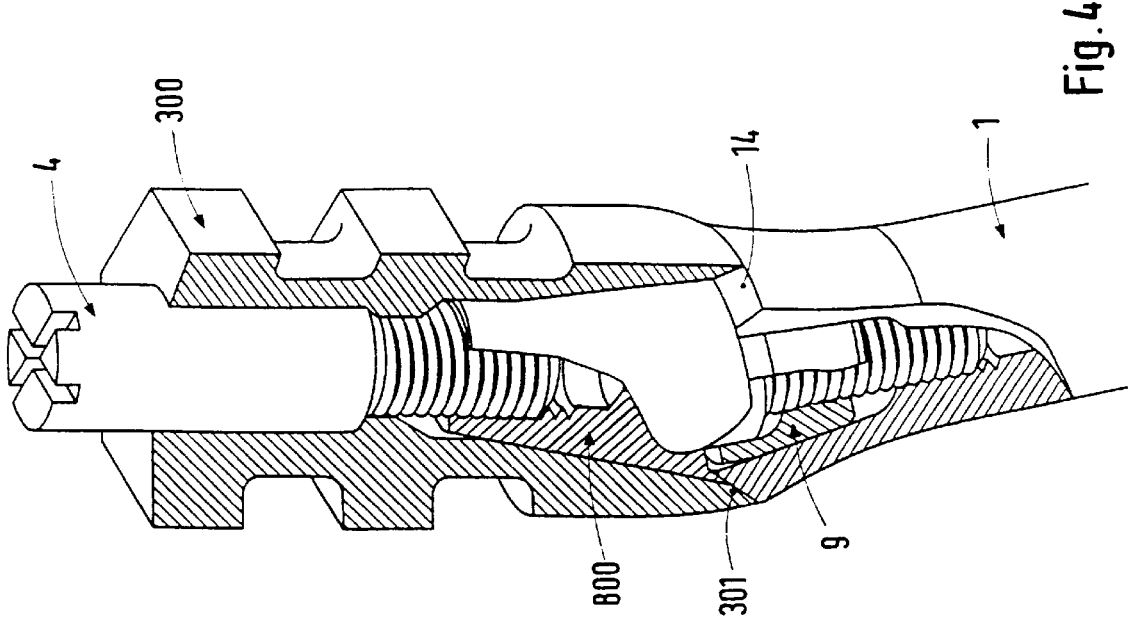
FIG. 4 shows an angled version of the connection arrangement in accordance with FIG. 2.

In the same way as FIG. 4 illustrates the angled version by comparison with FIG. 2, there is also a variant with an angled conical secondary part 800 which is analogous to FIG. 5 with the plug-on impression cap 300. Here too, the contours of the annular face 861 and of the mating shoulder 301 are to be adapted to the inclined position in accordance with the angle of the conical secondary part 800.

FIG. 7

After an impression has been taken in order to obtain the geometric constellation from the mouth of the patient, a manipulation implant 7 similar to the implant 1 is attached for further work on the impression acquired. In this state, the impression cap is embedded inside the impression, which in turn is surrounded by an impression tray. The figure shows the manipulation implant 7 with the conical secondary part 800, into the top side of which a plug-in anchor 100 is screwed, situated thereon. The manipulation implant 7 with the attached elements initially functions as a support for the impression in the production of the master model.

The conical secondary part 800 corresponds to the illustration in accordance with FIG. 3 and thus has the shoulder part 860 and the annular face 861. The manipulation implant 7, in a similar manner to the implant 1, has the head 71 with the implant shoulder 74. An axial, blind-bore-like threaded bore 72 with the exit-side, widened cylinder bore 75 is provided on the head 71. In the assembled state, the threaded segment 820 of the conical secondary part 800 engages in the threaded bore 72 and the base pillar 810 rests in a guided manner in the cylindrical bore 75. The annular face 861 of the shoulder part 860 partially bears on an inner, circular-ring-like zone of the implant shoulder 74. The threaded segment 110 of the plug-in anchor 100 is screwed into the threaded bore 840, the shank segment 120 of the plug-in anchor 100 resting to some extent in the countersinking 841. The free outer, circular-ring-like zone on the implant shoulder 74 serves to support the mating shoulder of the crown cap when producing the tooth crown.

FIG. 8

The finished tooth crown Zk is screwed occlusally to the conical secondary part 800 inserted into the implant 1. This requires an occlusal screw 400, in the form of a cap screw, and an access bore Zu through the porcelain coating Po which has been modelled onto the gold casting Go and through the crown cap 500, in order to provide access to the threaded bore 840 in the conical secondary part 800. A counterboring 530 is provided on the top side of the crown cap 500 to receive the head 420 of the occlusal screw 400. Once the screwing has been executed, the access bore Zu is sealed with a suitable composition. This access bore Zu is also used should it be necessary to remove the occlusal screw 400.

As already described above, the annular face 861 of the shoulder part 860 of the conical secondary part 800 bears partially on the implant shoulder 14. The remaining surface of the implant shoulder 14 is covered by the complementary mating shoulder 501 of the crown cap 500. Compared to the hitherto conventional attaching of a crown cap 500 on the implant shoulder 14, here only a partial area of the implant shoulder 14 is available to the mating shoulder 501 of the crown cap 500—similarly to the mating shoulder 301 of the impression cap 300.

FIG. 9

In contrast to FIG. 8, in this figure an angled conical secondary part 800 is screwed into the implant 1. Instead of the occlusal screwing, the finished tooth crown Zk is fastened to the enlarged conical pillar 830 by means of a layer of cement Ze, and it is not a prefabricated crown cap which is used but rather an individually cast metal crown, for example in the form of a gold casting Go.

It is possible to realize further variations, with regard to configuration and exchangeability, to the above-described modifications of the elements of the connection arrangement and to the possible combinations pointed out thus far. Those which are expressly mentioned are also:

The implant shoulders 14 and 74 could also have a chamfer other than 45°; the annular face 861 and the mating shoulders 301 and 501 of the impression cap 300 and of the crown cap 500, respectively, would then have to be produced with a correspondingly adapted positioning angle.

It is not absolutely necessary always to use the centring sleeve 9; this may be dispensed with. Then, however, the geometry of the base pillar 810 must be made conical, complementary to the implant cone 12.

The finished tooth crown Zk could also be fastened to the implant 14 in the mouth of the patient as a plug-in connection using the plug-in anchor 100 with a corresponding latching contour in the interior of the crown cap 500. It is also possible to produce the plug-in connections in the opposite manner, by fixing the plug-in anchors 100 facing downwards in the impression cap 300 or crown cap 500 and by situating the latching contour, by contrast, inside the conical secondary part 800.

Finally, it is possible to combine the connection arrangement with the transverse screwing already described in the parallel patent application.

We claim:

1. A connection arrangement for connecting an implant to a conical secondary part, comprising:

an implant having an implant head, which ends in an implant shoulder, and a base pillar support, with an axial blind-bore-like threaded bore;

a conical secondary part, including a threaded segment which engages said threaded bore, a base pillar which rests in said base pillar support, and a conical pillar which protrudes beyond said implant shoulder, said conical pillar being provided with a groove on an underside thereof, forming a shoulder part with an annular face of a configuration complementary to said implant shoulder such that said conical pillar rests on a portion of said implant shoulder beginning on an inner edge thereof; and a cap having a circular-ring-like mating shoulder of a configuration complementary to said implant shoulder such that said cap rests on a portion of said implant shoulder beginning at an outer edge of said conical secondary part.

2. A connection arrangement according to claim 1, wherein said implant is a dental implant and said base pillar support is a hollow implant cone.

3. A connection arrangement according to claim 1, wherein said implant is a manipulation implant and said base pillar support is a cylindrical bore.

4. A connection arrangement according to claim 1, further comprising a centering sleeve which is inserted into said base pillar support, to provide additional centering to said conical secondary part.

5. A connection arrangement according to claim 1, wherein said cap is an impression cap used for taking impressions, producing a master model, and building up and fixing a finished tooth crown on said implant.

6. A connection arrangement according to claim 1, wherein said cap is a prefabricated crown cap.

7. A connection arrangement according to claim 1, wherein said cap is an individually cast metal crown.

8. A connection arrangement according to claim 1, wherein said implant shoulder and said annular face of said conical secondary part have an angle of inclination to the horizontal which is not equal to 0 degrees.

9. A connection arrangement according to claim 8, wherein said angle of inclination is 45 degrees.

10. A connection arrangement according to claim 1, wherein said conical secondary part is further provided with an axial blind-bore-like threaded bore in said conical pillar to accommodate a threaded segment of a connecting part for connecting said cap to said conical secondary part.

11. A connection arrangement according to claim 10, wherein said connecting part is a positioning screw.

12. A connection arrangement according to claim 10, wherein said connecting part is an occlusal screw.

13. A connection arrangement according to claim 10, wherein said connecting part is a plug-in anchor and said conical secondary part is further provided with a countersink to accommodate a collar of said plug-in anchor.

14. A connection arrangement according to claim 10, wherein said conical secondary part has a rotationally symmetrical configuration.

15. A connection arrangement according to claim 10, wherein said conical secondary part has an angled configuration.

* * * * *